(12) United States Patent
Kampa (10) Patent No.: US 7,776,034 B2
(45) Date of Patent: Aug. 17, 2010

(54) ABLATION CATHETER WITH ADJUSTABLE VIRTUAL ELECTRODE

(75) Inventor: Gregory J. Kampa, Blaine, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1117 days.

(21) Appl. No.: 11/154,098

(22) Filed: Jun. 15, 2005

(65) Prior Publication Data

US 2007/0005051 A1  Jan. 4, 2007

(51) Int. Cl.
*A61B 18/14* (2006.01)
(52) U.S. Cl. .......................................................... 606/41
(58) Field of Classification Search .................. 606/32, 606/41; 607/80, 104, 105
See application file for complete search history.

(56) References Cited

U.S. PATENT DOCUMENTS

| | | | | |
|---|---|---|---|---|
| 3,911,902 A | * | 10/1975 | Delpy | 600/488 |
| 4,329,994 A | * | 5/1982 | Cooper | 604/98.01 |
| 4,407,304 A | * | 10/1983 | Lieber et al. | 607/122 |
| 4,945,912 A | | 8/1990 | Langberg | |
| 5,281,213 A | | 1/1994 | Milder et al. | 606/15 |
| 5,281,217 A | * | 1/1994 | Edwards et al. | 606/41 |
| 5,334,193 A | | 8/1994 | Nardella | 606/41 |
| 5,370,644 A | | 12/1994 | Langberg | |
| 5,431,649 A | | 7/1995 | Mulier et al. | 606/41 |
| 5,433,708 A | | 7/1995 | Nichols et al. | 604/113 |
| 5,542,434 A | * | 8/1996 | Imran et al. | 600/585 |
| 5,542,928 A | | 8/1996 | Evans et al. | 604/113 |
| 5,584,872 A | | 12/1996 | LaFontaine et al. | 607/116 |
| 5,609,151 A | | 3/1997 | Mulier et al. | 128/642 |
| 5,658,278 A | | 8/1997 | Imran et al. | 600/41 |
| 5,676,693 A | | 10/1997 | LaFontaine | 607/116 |
| 5,697,927 A | | 12/1997 | Imran et al. | 606/41 |
| 5,725,524 A | | 3/1998 | Mulier et al. | 606/41 |
| 5,785,706 A | * | 7/1998 | Bednarek | 606/41 |
| 5,876,398 A | | 3/1999 | Mulier et al. | 606/41 |
| 5,895,417 A | | 4/1999 | Pomeranz et al. | 607/101 |
| 5,913,854 A | | 6/1999 | Maguire et al. | 606/41 |
| 5,913,856 A | | 6/1999 | Chia et al. | 606/41 |
| 5,919,188 A | * | 7/1999 | Shearon et al. | 606/41 |
| 5,921,954 A | * | 7/1999 | Mohr et al. | 604/508 |
| 5,971,968 A | * | 10/1999 | Tu et al. | 604/264 |
| 5,997,532 A | | 12/1999 | McLaughlin et al. | 606/41 |
| 6,010,500 A | * | 1/2000 | Sherman et al. | 606/41 |
| 6,015,407 A | * | 1/2000 | Rieb et al. | 606/41 |
| 6,016,809 A | | 1/2000 | Mulier et al. | 128/898 |

(Continued)

*Primary Examiner*—Lee S Cohen
(74) *Attorney, Agent, or Firm*—Heimbecher & Assoc., LLC (57) ABSTRACT

An ablation catheter has a virtual electrode tip including a fluid manifold structure for operably varying the active area of the virtual electrode. An array of apertures in the distal end of the catheter form the virtual electrode structure. A movable plug slides within the fluid manifold and seals against the interior walls of the fluid manifold. Conductive fluid cannot flow past the plug to fill the fluid manifold on the side of the plug opposite a fluid inlet channel into the fluid manifold. An electrode is positioned within the fluid manifold between the plug and the end wall of the fluid manifold adjacent the channel. By moving the plug within fluid manifold, only those portholes between the plug and the inlet channel will emit energized fluid. The effective length of an active ablation section of the virtual electrode is changed by repositioning the plug within the fluid manifold.

20 Claims, 7 Drawing Sheets

U.S. PATENT DOCUMENTS

| | | | |
|---|---|---|---|
| 6,032,077 A * | 2/2000 | Pomeranz | 607/101 |
| 6,044,846 A * | 4/2000 | Edwards | 128/898 |
| 6,063,080 A | 5/2000 | Nelson et al. | 606/41 |
| 6,068,653 A | 5/2000 | LaFontaine | 607/116 |
| 6,080,151 A * | 6/2000 | Swartz et al. | 606/45 |
| 6,119,041 A | 9/2000 | Pomeranz et al. | 607/101 |
| 6,120,476 A | 9/2000 | Fung et al. | 604/95 |
| 6,120,500 A * | 9/2000 | Bednarek et al. | 606/41 |
| 6,132,405 A * | 10/2000 | Nilsson et al. | 604/264 |
| 6,132,426 A | 10/2000 | Kroll | 606/41 |
| 6,168,594 B1 | 1/2001 | LaFontaine et al. | 606/41 |
| 6,171,275 B1 | 1/2001 | Webster, Jr. | 604/20 |
| 6,217,576 B1 | 4/2001 | Tu et al. | 606/41 |
| 6,219,582 B1 | 4/2001 | Hofstad et al. | 607/122 |
| 6,235,022 B1 | 5/2001 | Hallock et al. | 606/41 |
| 6,235,044 B1 | 5/2001 | Root et al. | 606/200 |
| 6,238,393 B1 | 5/2001 | Mulier et al. | 606/41 |
| 6,241,722 B1 | 6/2001 | Dobak et al. | 606/23 |
| 6,264,654 B1 * | 7/2001 | Swartz et al. | 606/45 |
| 6,409,722 B1 | 6/2002 | Hoey et al. | 606/34 |
| 6,454,766 B1 | 9/2002 | Swanson et al. | 696/41 |
| 6,522,930 B1 * | 2/2003 | Schaer et al. | 607/101 |
| 6,605,087 B2 * | 8/2003 | Swartz et al. | 606/41 |
| 6,607,505 B1 * | 8/2003 | Thompson et al. | 604/95.04 |
| 6,702,811 B2 | 3/2004 | Stewart et al. | |
| 6,858,026 B2 | 2/2005 | Sliwa et al. | 606/28 |
| 6,960,207 B2 * | 11/2005 | Vanney et al. | 606/41 |
| 6,984,232 B2 * | 1/2006 | Vanney et al. | 606/41 |
| 7,087,053 B2 * | 8/2006 | Vanney | 606/41 |
| 7,101,362 B2 * | 9/2006 | Vanney | 604/523 |
| 7,235,070 B2 * | 6/2007 | Vanney | 606/41 |
| 7,326,208 B2 * | 2/2008 | Vanney et al. | 606/41 |
| 2004/0181189 A1 | 9/2004 | Roychowdhury et al. | |
| 2005/0055019 A1 | 3/2005 | Skarda | |

* cited by examiner

ABLATION CATHETER WITH ADJUSTABLE VIRTUAL ELECTRODE

BACKGROUND OF THE INVENTION a. Field of the Invention

The instant invention is directed toward a catheter with a virtual electrode section including a fluid distribution structure for ablation of tissue. The length of an active area of the electrode section is variable by adjusting the size of a fluid manifold.

b. Background Art

A catheter is generally a very small diameter tube for insertion into the body for the performance of medical procedures. Among other uses, catheters can be used to examine, diagnose, and treat while positioned at a specific location within the body that is otherwise inaccessible without more invasive procedures. During these procedures a catheter is inserted into the patient's vasculature near the surface of the body and is guided to a specific location within the body for examination, diagnosis, and treatment. For example, one procedure utilizes a catheter to convey an electrical stimulus to a selected location within the human body. Another procedure utilizes a catheter with sensing electrodes to monitor various forms of electrical activity in the human body.

Catheters are used increasingly for these types of medical procedures involving the human heart. Typically, the catheter is inserted in an artery or vein in the leg, neck, or arm of the patient and threaded, sometimes with the aid of a guide wire or introducer, through the vasculature until a distal tip of the catheter reaches the desired location for the medical procedure in the heart.

A typical human heart includes a right ventricle, a right atrium, a left ventricle, and a left atrium. The right atrium is in fluid communication with the superior vena cava and the inferior vena cava. The atrioventricular septum separates the right atrium from the right ventricle. The tricuspid valve contained within the atrioventricular septum provides communication between the right atrium and the right ventricle.

In the normal heart, contraction and relaxation of the heart muscle (myocardium) takes place in an organized fashion as electro-chemical signals pass sequentially through the myocardium from the sinoatrial (SA) node, which comprises a bundle of unique cells disposed in the wall of the right atrium, to the atrioventricular (AV) node and then along a well-defined route, which includes the His-Purkinje system, into the right and left ventricles. The AV node lies near the ostium of the coronary sinus in the interatrial septum in the right atrium. Each cell membrane of the SA node has a characteristic tendency to leak sodium ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole, wherein the atria contract to empty and fill blood into the ventricles. The atrial depolarization from the SA node is detected by the AV node which, in turn, communicates the depolarization impulse into the ventricles via the bundle of His and Purkinje fibers following a brief conduction delay. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches that straddle the summit of the muscular part of the interventricular septum.

Sometimes abnormal rhythms occur in the heart, which are referred to generally as arrhythmia. For example, a common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle.

Other abnormal arrhythmias sometimes occur in the atria, which are referred to as atrial arrhythmia. Three of the most common atrial arrhythmia are ectopic atrial tachycardia, atrial fibrillation, and atrial flutter. Atrial fibrillation can result in significant patient discomfort and even death because of a number of associated problems, including the following: an irregular heart rate, which causes patient discomfort and anxiety; loss of synchronous atrioventricular contractions, which compromises cardiac hemodynamics, resulting in varying levels of congestive heart failure; and stasis of blood flow, which increases the likelihood of thromboembolism.

Efforts to alleviate these problems in the past have included significant usage of pharmacological treatments. While pharmacological treatments are sometimes effective, in some circumstances drug therapy has had only limited effectiveness and is frequently plagued with side effects, such as dizziness, nausea, vision problems, and other difficulties.

An increasingly common medical procedure for the treatment of certain types of cardiac arrhythmia is catheter ablation. During conventional catheter ablation procedures, an energy source is placed in contact with cardiac tissue to heat the tissue and create a permanent scar or lesion that is electrically inactive or noncontractile. During one procedure, the lesions are designed to interrupt existing conduction pathways commonly associated with arrhythmias within the heart. The particular area for ablation depends on the type of underlying arrhythmia. One common ablation procedure treats atrioventricular nodal reentrant tachycardia (AVNRT). Ablation of fast or slow AV nodal pathways is disclosed in Singer, I., et al., "Catheter Ablation for Arrhythmias," Clinical Manual of Electrophysiology, pgs. 421-431 (1993).

Another medical procedure using ablation catheters with sheaths to ablate accessory pathways associated with W-P-W utilizing both a transseptal and retrograde approach is discussed in Saul, J. P., et al., "Catheter Ablation of Accessory Atrioventricular Pathways in Young Patients: Use of long vascular sheaths, the transseptal approach and a retrograde left posterior parallel approach," Journal of the American College of Cardiology, Vol. 21, no. 3, pgs. 571-583 (1 Mar. 1993). Other catheter ablation procedures are disclosed in Swartz, J. F., "Radiofrequency Endocardial Catheter Ablation of Accessory Atrioventricular Pathway Atrial Insertion Sites," Circulation, Vol. 87, no. 2, pgs. 487-499 (February 1993).

Ablation of a specific location within or near the heart requires the precise placement of the ablation catheter. Precise positioning of the ablation catheter is especially difficult because of the physiology of the heart, particularly because the heart continues to beat throughout the ablation procedures. Commonly, the choice of placement of the catheter is determined by a combination of electrophysiological guidance and fluoroscopy. Fluoroscopy, in a relevant form, involves the placement of the catheter in relation to known features of the heart, which are marked by radiopaque diagnostic catheters that are placed in or at known anatomical structures, such as the coronary sinus, high right atrium, and the right ventricle).

The energy necessary to ablate cardiac tissue and create a permanent lesion can be provided from a number of different sources. Originally, direct current was utilized although laser, microwave, ultrasound, and other forms of energy have also been utilized to perform ablation procedures. Because of problems associated with the use of direct current, however, radio frequency (RF) has become the preferred source of energy for ablation procedures. The use of RF energy with an ablation catheter contained within a transseptal sheath for the treatment of W-P-W in the left atrium is disclosed in Swartz, J. F. et al., "Radiofrequency Endocardial Catheter Ablation of Accessory Atrioventricular Pathway Atrial Insertion Sites," Circulation, Vol. 87, pgs. 487-499 (1993). See also Tracey, C. N., "Radio Frequency Catheter Ablation of Ectopic Atrial Tachycardia Using Paced Activation Sequence Mapping," J. Am. Coll. Cardiol. Vol. 21, pgs. 910-917 (1993).

In addition to RF ablation catheters, thermal ablation catheters have been used. During thermal ablation procedures, a heating element, secured to the distal end of a catheter, heats thermally conductive fluid, which fluid then contacts the human tissue to raise its temperature for a sufficient period of time to ablate the tissue.

Conventional ablation procedures utilize a single distal electrode secured to the tip of an ablation catheter. Increasingly, however, cardiac ablation procedures utilize multiple electrodes affixed to the catheter body. These ablation catheters often contain a distal tip electrode and a plurality of ring electrodes.

To form linear lesions within the heart using a conventional ablation tip electrode requires the utilization of procedures such as a "drag burn." The term "linear lesion" as used herein means an elongate, continuous lesion, whether straight or curved, that blocks electrical conduction. During a "drag burn" procedure, while ablating energy is supplied to the tip electrode, the tip electrode is drawn across the tissue to be ablated, producing a line of ablation. Alternatively, a series of points of ablation are formed in a line created by moving the tip electrode incremental distances across the cardiac tissue. The effectiveness of these procedures depends on a number of variables including the position and contact pressure of the tip electrode of the ablation catheter against the cardiac tissue, the time that the tip electrode of the ablation catheter is placed against the tissue, the amount of coagulum that is generated as a result of heat generated during the ablation procedure, and other variables associated with a beating heart, especially an erratically beating heart. Unless an uninterrupted track of cardiac tissue is ablated, unablated tissue or incompletely ablated tissue may remain electrically active, permitting the continuation of the stray circuit that causes the arrhythmia.

It has been discovered that more efficient ablation may be achieved if a linear lesion of cardiac tissue is formed during a single ablation procedure. The ablation catheters commonly used to perform these ablation procedures produce electrically inactive or noncontractile tissue at a selected location by physical contact of the cardiac tissue with an electrode of the ablation catheter. Conventional tip electrodes with adjacent ring electrodes cannot perform this type of procedure, however, because of the high amount of energy that is necessary to ablate sufficient tissue to produce a complete linear lesion. Also, conventional ring electrode ablation may leave holes or gaps in a lesion, which can provide a pathway along which unwanted electrochemical signals can travel.

During conventional ablation procedures, the ablating energy is delivered directly to the cardiac tissue by an electrode on the catheter placed against the surface of the tissue to raise the temperature of the tissue to be ablated. This rise in tissue temperature also causes a rise in the temperature of blood surrounding the electrode. This often results in the formation of coagulum on the electrode, which reduces the efficiency of the ablation electrode. With direct contact between the electrode and the blood, some of the energy targeted for the tissue ablation is dissipated into the blood. To achieve efficient and effective ablation, coagulation of blood that is common with conventional ablation catheters should be avoided. This coagulation problem can be especially significant when linear ablation lesions or tracks are produced because such linear ablation procedures conventionally take more time than ablation procedures ablating only a single location.

To address the coagulation concern, more recent designs of ablation electrodes transfer energy to the target tissue with a conductive fluid medium that passes over a standard metal electrode rather than contacting the standard electrode to the tissue. The fluid flow thus reduces the likelihood that coagulum will form on any of the surfaces of the electrode. These so-called "virtual electrodes" also help reduce tissue charring because the fluid, while energized, also acts as a cooling heat transfer medium. However, with present virtual electrode designs, the fluid flow is not often uniform, resulting in hot spots due to greater energy transfer in areas with greater flow. Further, with present virtual electrode designs, the volume of fluid flow required to create a lesion is very high and thus introduces a significant amount of excess fluid into the patient's vasculature, which can significantly dilute the patient's blood volume and compromise pulmonary circulation capacity.

In some instances, stray electrical signals find a pathway down the pulmonary veins and into the left atrium of the heart. In these instances, it may be advantageous to produce a circumferential lesion at or near the ostium of one or more of the pulmonary veins. Desirably, such a circumferential lesion would electrically isolate a pulmonary vein from the left atrium, completely blocking stray signals from traveling down the pulmonary vein and into the left atrium. It is desirable to have a catheter with a distal portion for forming such circumferential lesions in tissue while avoiding problems with existing designs.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

The present invention is directed to an ablation catheter with a virtual electrode tip, which includes a fluid manifold structure that allows a clinician to vary length of the active area of the virtual electrode. Conductive fluid is carried in the catheter within a main fluid lumen and then is transferred to the fluid lumen via an inlet channel at the distal end of the catheter. An array of portholes in the distal end of the catheter form the virtual electrode structure. Each porthole may be a combination of a blind hole in the catheter wall encompassing an array of weep holes extending through the catheter wall into the fluid manifold. A movable plug slides within the fluid manifold and also seals against the interior walls of the fluid manifold, thereby preventing the conductive fluid from flowing past the plug to an area of the fluid manifold on the side of the plug opposite the inlet channel. An electrode is positioned within the fluid manifold between the plug and the end wall of the fluid manifold adjacent the channel in order to energize the conductive fluid. By moving the plug within fluid manifold, only those portholes between the present position of the plug and the inlet channel will emit energized fluid. In this manner the effective length of an active ablation section of the virtual electrode can be changed by repositioning the plug within the fluid manifold.

In one embodiment of the invention, a catheter has an exterior catheter wall, a proximal section, and an ablation section at a distal end of the catheter. An interior catheter wall at least partially defines a fluid lumen extending from the proximal section to the ablation section. A fluid manifold is at least partially defined by the interior catheter wall and the exterior catheter wall. The fluid manifold is positioned in the ablation section adjacent to the fluid lumen and is separated from the fluid lumen by the interior wall. The interior wall further defines a channel between the fluid lumen and the fluid manifold. An array of a plurality of apertures is defined within the exterior catheter wall adjacent to the fluid manifold and in fluid communication with the fluid manifold. An electrode and a movable sealing plug are also positioned within the fluid manifold. An actuator is attached to the movable sealing plug for repositioning the plug within the fluid manifold.

In another embodiment of the invention, a catheter has an exterior catheter wall, a proximal section, and an ablation section at a distal end of the catheter. An interior catheter wall at least partially defines a fluid lumen extending from the proximal section to the ablation section. A fluid manifold is at least partially defined by the interior catheter wall and the exterior catheter wall. The fluid manifold is positioned in the ablation section adjacent to the fluid lumen and is separated from the fluid lumen by the interior wall. The interior wall further defines a channel between the fluid lumen and the fluid manifold. An array of a plurality of blind holes defined in an exterior surface of the exterior catheter wall adjacent to the fluid manifold. At least one weep hole is circumscribed by each blind hole and the at least one weep hole is in fluid communication with both the fluid manifold and the respective circumscribing blind hole. A movable sealing plug is positioned within the fluid manifold and a coil spring electrode is positioned between the movable sealing plug and a position of the channel in the fluid manifold. A first end of the coil spring electrode is attached to the movable sealing plug and a second end of the coil spring electrode is attached to an end wall of the fluid manifold. An adjustment shaft extends from the proximal section of the catheter to the ablation section and a distal end of the adjustment shaft is attached to the movable sealing plug. The distal end of the adjustment shaft is translatable proximally and distally along a length of the fluid manifold and thereby repositions the plug within the fluid manifold.

In an alternative embodiment of the invention, a catheter has an exterior catheter wall, a proximal section, and an ablation section at a distal end of the catheter. An interior catheter wall at least partially defines a fluid lumen extending from the proximal section to the ablation section. A fluid manifold is at least partially defined by the interior catheter wall and the exterior catheter wall. The fluid manifold is positioned in the ablation section adjacent to the fluid lumen and is separated from the fluid lumen by the interior wall. The interior wall further defines a channel between the fluid lumen and the fluid manifold. An array of a plurality of blind holes is defined in an exterior surface of the exterior catheter wall adjacent to the fluid manifold. At least one weep hole is circumscribed by each blind hole and the at least one weep hole is in fluid communication with the fluid manifold and the respective circumscribing blind hole. A movable sealing plug is positioned within the fluid manifold and a coil spring electrode is positioned between the movable sealing plug and a position of the channel in the fluid manifold. A first end of the coil spring electrode is attached to the movable sealing plug and a second end of the coil spring electrode is attached to an end wall of the fluid manifold. A first pull wire extends from the proximal section of the catheter to the ablation section and a second pull wire also extends from the proximal section of the catheter to the ablation section. A pulley is mounted at the distal end of the fluid manifold. A distal end of the first pull wire is fixed to a proximal side of the movable sealing plug. A distal end of the second pull wire is fixed to a distal side of the movable sealing plug. The second pull wire extends distally through an aperture in the movable sealing plug and engages the pulley before the distal end of the second pull wire is fixed to the movable sealing plug.

In yet another embodiment, the invention involves a method for varying the length of an active portion of a virtual electrode section of an ablation catheter. A movable plug is positioned within a fluid manifold in the virtual electrode section. The movable plug seals against the fluid manifold to prevent fluid flow within the fluid manifold from one side of the movable plug to the other side of the movable plug. A conductive fluid is introduced at one end of the fluid manifold. The conductive fluid flows out of the fluid manifold through a plurality of apertures in an exterior wall of the ablation catheter. Each of the plurality of apertures is in fluid communication with the fluid manifold. The movable plug is then repositioned within the fluid manifold to prevent the conductive fluid from flowing through a subset of the plurality of apertures.

Other features, details, utilities, and advantages of the present invention will be apparent from the following more particular written description of various embodiments of the invention as further illustrated in the accompanying drawings and defined in the appended claims.

DETAILED DESCRIPTION OF THE INVENTION

The present invention concerns an improved design for ablation catheters used, for example, in cardiac ablation procedures to produce linear lesions in cardiac tissue. The electrode structure on the distal end of the catheter of the present invention is generally termed a "virtual electrode." In a virtual electrode design, ablation energy is primarily imparted to the target tissue via energy transfer through a conductive fluid medium escaping the distal end of the catheter rather than by actual contact of a traditional electrode with the tissue. The present invention is primarily directed to providing a variable length virtual electrode to allow a clinician to create lesions of varying length in the target tissue.

Figure 1:
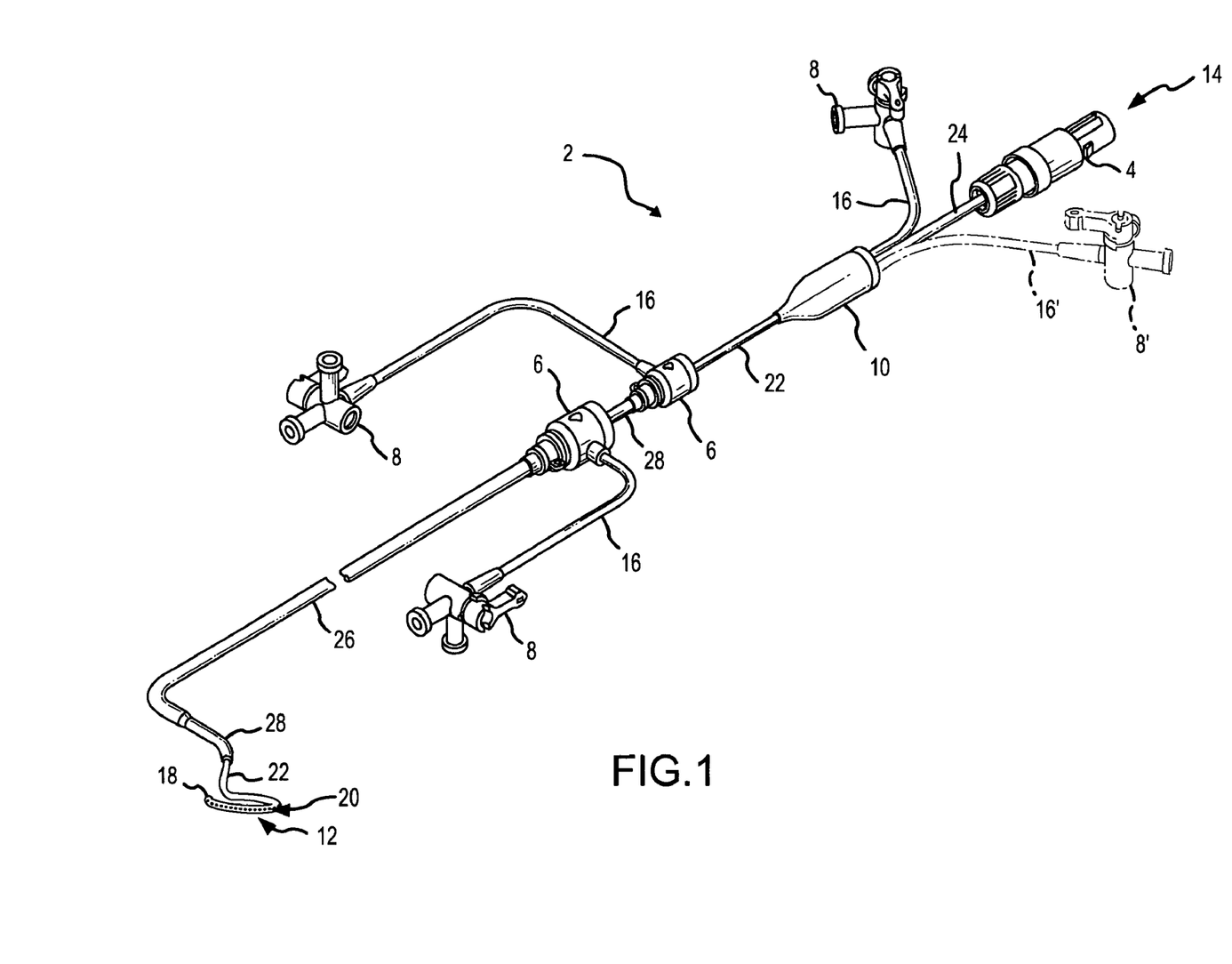
FIG. 1 is an isometric view of a ablation catheter/introducer assembly including an electrode tip according to a generic embodiment of the present invention.

FIG. 1 is an isometric view of a catheter/introducer assembly 2 for use in conjunction with the present invention. A catheter 22 with a handle interface 4 at a proximal end 14 and an ablation electrode section 20, according to a generic embodiment of the present invention, at a distal end 12 is used in combination with an inner guiding introducer 28 and an outer guiding introducer 26 to facilitate formation of lesions on tissue, for example, cardiovascular tissue. The inner guiding introducer 28 is longer than and is inserted within the lumen of the outer guiding introducer 26. Alternatively, a single guiding introducer or a precurved transeptal sheath may be used instead of both the inner guiding introducer 28 and the outer guiding introducer 26. In general, introducers or precurved sheaths are shaped to facilitate placement of the ablation electrode section 20 at the tissue surface to be ablated. As depicted in FIG. 1, for example, the outer guiding introducer 26 may be formed with a curve at the distal end 12. Similarly, the inner guiding introducer 28 may be formed with a curve at the distal end 12. Together, the curves in the guiding introducers 26, 28 help orient the catheter 22 as it emerges from the inner guiding introducer 26 in a cardiac cavity. Thus, the inner guiding introducer 28 and the outer guiding introducer 26 are used navigate a patient's vasculature to the heart and through its complex physiology to reach specific tissue to be ablated. The guiding introducers 26, 28 need not be curved or curved in the manner depicted depending upon the desired application.

As shown in FIG. 1, each of the guiding introducers 26, 28 is connected with a hemostatic valve 6 at its proximal end to prevent blood or other fluid that fills the guiding introducers 26, 28 from leaking before the insertion of the catheter 22. The hemostatic valves 6 form tight seals around the shafts of the guiding introducers 26, 28 or the catheter 22 when inserted therein. Each hemostatic valve 6 may be have a port connected with a length of tubing 16 to a fluid introduction valve 8. The fluid introduction valves 8 may be connected with a fluid source, for example, saline or a drug, to easily introduce the fluid into the introducers, for example, to flush the introducer or to inject a drug in to the patient. Each of the fluid introduction valves 8 may control the flow of fluid into the hemostatic valves 16 and thereby the guiding introducers 26, 28.

The proximal end 14 of the catheter 22 may include a catheter boot 10 that seals around several components to allow the introduction of fluids and control mechanisms into the catheter 22. For example, at least one fluid introduction valve 8 with an attached length of tubing 16 may be coupled with the catheter boot 10. An optional fluid introduction valve 8' and correlative tube 16' (shown in phantom) may also be coupled with the catheter boot 10, for example, for the introduction of fluid into a catheter with multiple fluid lumens if separate control of the pressure and flow of fluid in the separate lumens is desired. A handle interface 4 for connection with a control handle, a generator, and/or sensing equipment (none shown) may be coupled with the catheter boot 10 via a control shaft 24. The control shaft 24 may enclose, for example, control wires for manipulating the catheter 22 or ablation electrode section 20, conductors for energizing an electrode in the ablation electrode section 20, and/or lead wires for connecting with sensors in the ablation electrode section 20. The catheter boot 10 provides a sealed interface to shield the connections between such wires and fluid sources and one or more lumen in the catheter 22 through which they extend.

The distal end of the catheter may be straight or take on a myriad of shapes depending upon the desired application. The distal end 12 of one embodiment of a catheter 22 according to the present invention is shown in greater detail in FIGS. 2 and 3. In the embodiment shown in FIGS. 2 and 3, the catheter 22 consists mainly of a "straight" section 30 extending from the catheter boot 10 at the proximal end 14 to a point adjacent to the distal end 12 of the catheter/introducer assembly 2 (see the exemplary catheter of FIG. 1). At the distal end 12 the catheter 22 is composed of a first curved section 32 and a second curved section 34 before transitioning into a third curved section 36 that forms the ablation electrode. The first curved section 32 is adjacent and distal to the straight section 30 and proximal and adjacent to the second curved section 34. The second curved section 34 is itself proximal and adjacent to the third curved section 36. The straight section 30, first curved section 32, second curved section 34, and third curved section 36 may together form a single, unitary structure of the catheter 22, but may originally be separate pieces joined together to form the catheter 22.

Each of the different sections of the catheter may be constructed from a number of different polymers, for example, polypropylene, oriented polypropylene, polyethylene, polyethylene terephthalate, crystallized polyethylene terephthalate, polyester, polyvinyl chloride, polytetraflouroethylene (PTFE), expanded polytetraflouroethylene (ePTFE), and Pellethane. Alternatively, the different sections of the catheter may be composed, for example, of different formulations of Pebax® resins (AUTOFINA Chemicals, Inc., Philadelphia, Pa.), or other polyether-block co-polyamide polymers, which can be used to create desired materials stiffness within the different sections of the catheter. By using different formulations of the Pebax® resins, different mechanical properties (e.g., flexibility or stiffness) can be chosen for each of the sections along the catheter.

The catheter may also be a braided catheter wherein the catheter wall includes a cylindrical and/or flat braid of metal fibers (not shown), for example, stainless steel fibers. Such a metallic braid may be included in the catheter to add stability to the catheter and also to resist radial forces that might crush the catheter. Metallic braid also provides a framework to translate torsional forces imparted by the clinician on the proximal end of the catheter to the distal end to rotate the catheter for appropriate orientation of the ablation electrode.

Figure 2:
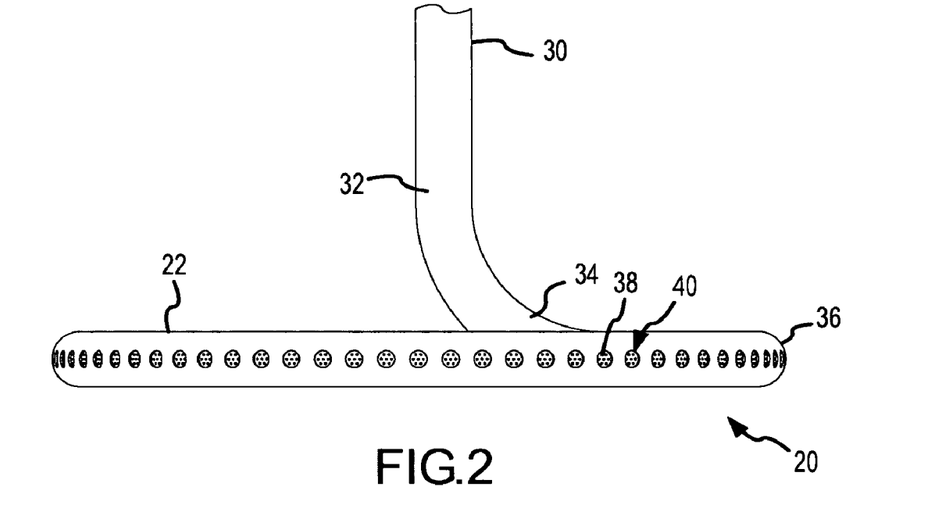
FIG. 2 is an elevation view of a distal portion of a catheter, including a virtual electrode tip, according to one embodiment of the present invention.
Figure 3:
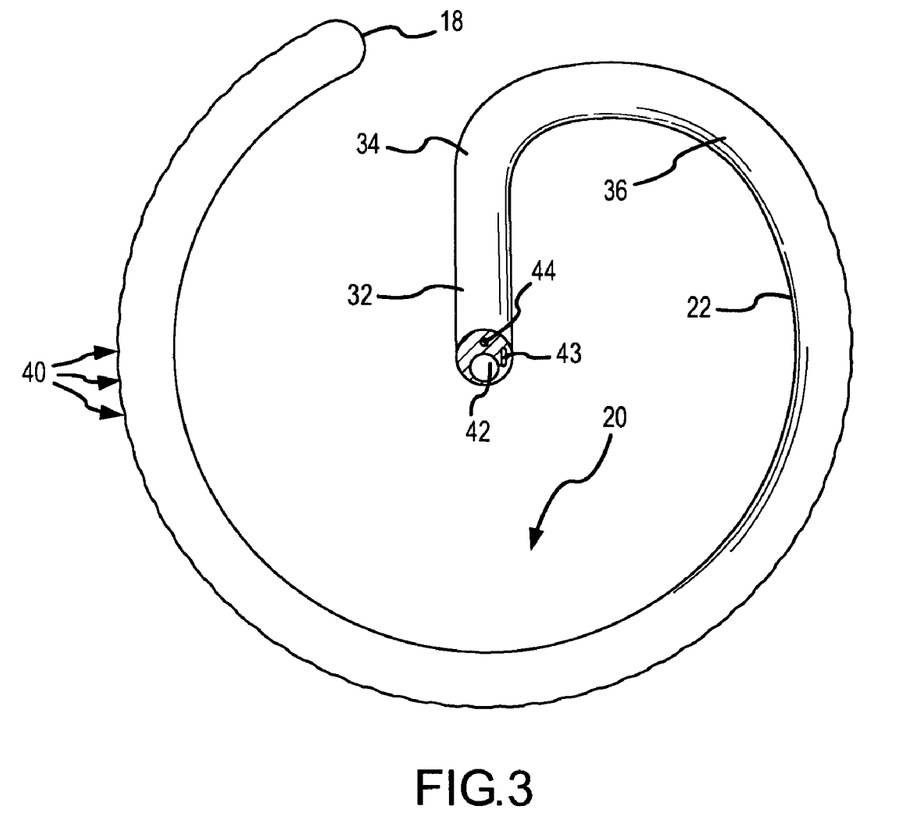
FIG. 3 is a top plan view of the catheter of FIG. 2.

The straight section 30 is generally the portion of the catheter 22 that remains within the vasculature of the patient while a sensing or ablation procedure is performed by a clinician. As shown in FIGS. 2 and 3, the ablation electrode section 20 may assume a generally circular or C-shaped configuration when deployed from the inner guiding introducer 28. The first curved section 32 and second curved section 34 of the catheter 22 align the straight section 30 of the catheter 22 with respect to the third curved section 36. In particular, the distal end of the straight section 30 of the catheter 22 is oriented in a position where a longitudinal axis extending through the distal end of the straight section 30 passes orthogonally through the center of a circle defined by the C-shaped third curved section 36. In this manner the straight section 30 of the catheter 122 is spatially displaced from the ablation electrode section 120 so that the straight section 30 is unlikely to interfere with the interface between the ablation electrode on the third curved section 36 and the cardiac tissue as further described below.

Figure 4:
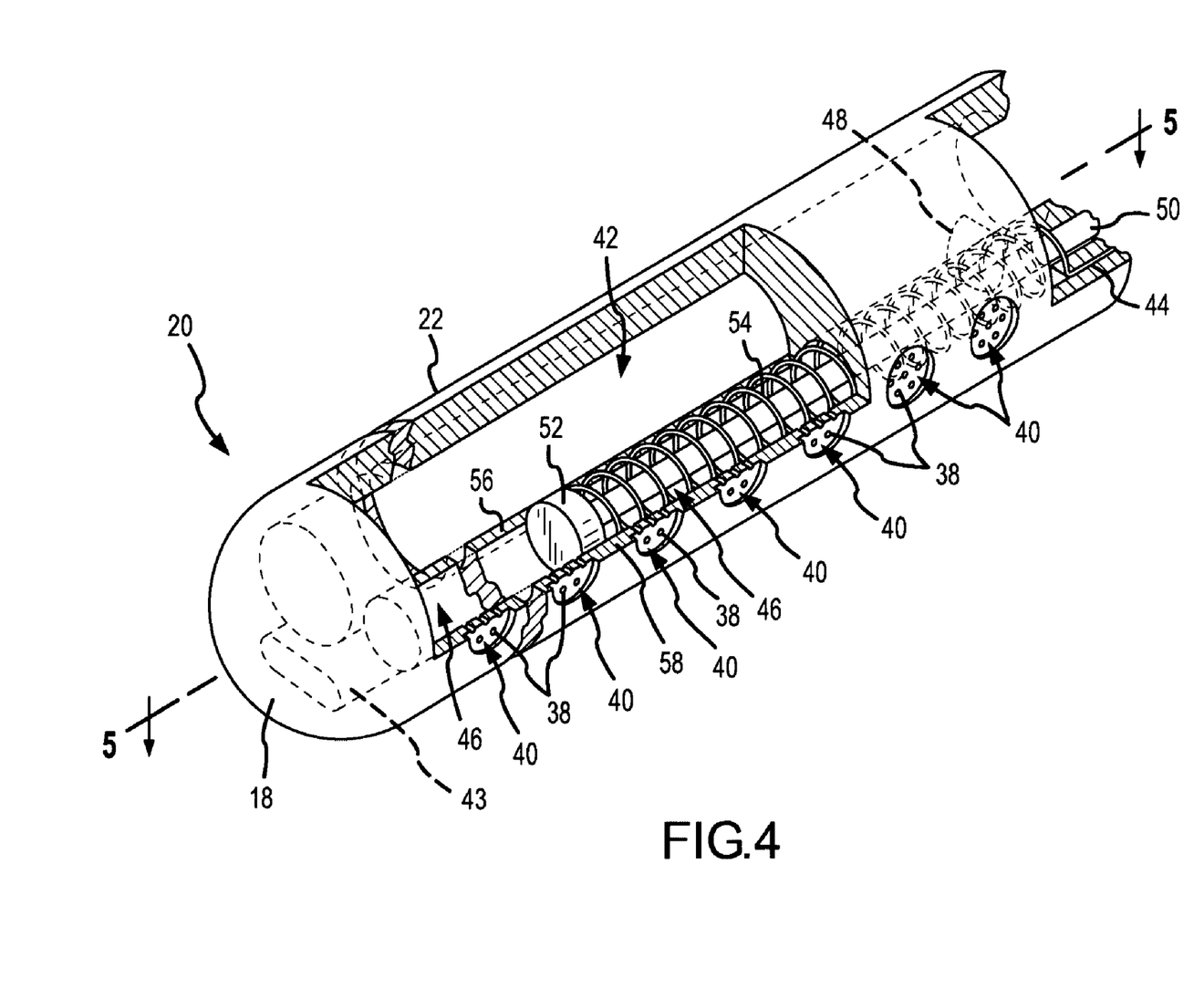
FIG. 4 is an isometric view with a partial cut-away of the distal end of the catheter of FIG. 2.
Figure 5:
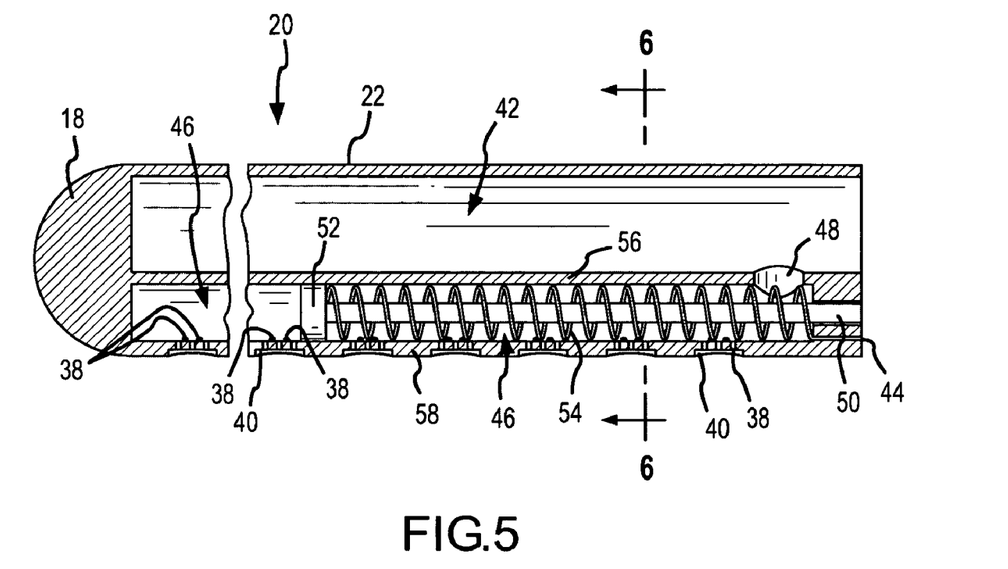
FIG. 5 is a cross-section view of the catheter of FIG. 2 taken along line 5-5 as indicated in FIG. 4.
Figure 6:
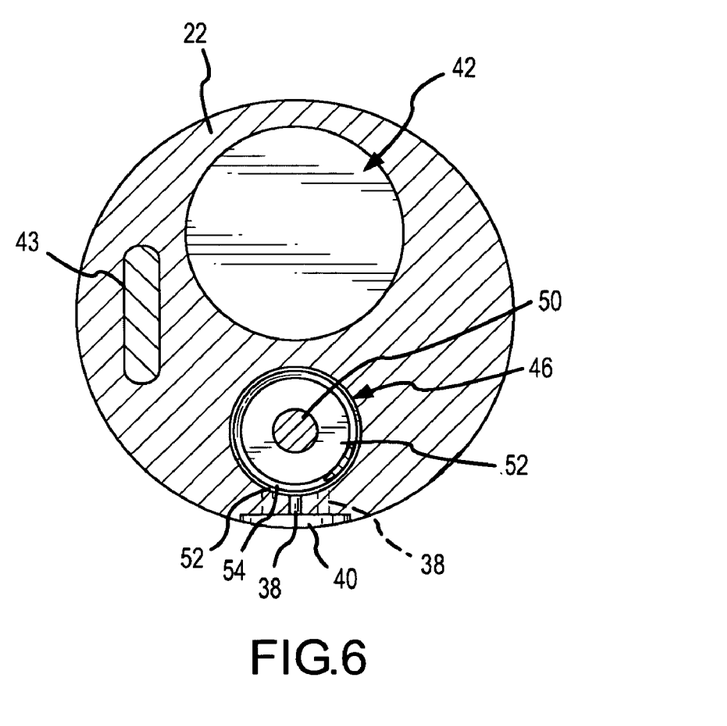
FIG. 6 is a cross-section view of the catheter of FIG. 2 taken along line 6-6 as indicated in FIG. 5.

FIGS. 4, 5, and 6 depict in greater detail the mechanism for creating a variable length ablation electrode 20 according to one embodiment of the present invention. The catheter 22 defines a fluid lumen 42 that extends the entire length of the catheter 22 from the proximal end 14 at the catheter boot 10 to the ablation electrode section 20 where it is capped by the distal tip 18 of the catheter 22. The distal end 12 of the catheter 22 also defines a second lumen in the form of a fluid manifold 46. The fluid manifold 46 generally extends only the length of the ablation electrode section 20 of the catheter 22. The fluid lumen 42 and the fluid manifold 46 are separated by an interior wall 56. The fluid lumen 42 and the fluid manifold 46 are fluidly connected at the proximal end of the fluid manifold 46 via a transverse inlet channel 48. The transverse inlet channel 48 communicates fluid, for example, a conductive fluid such as isotonic saline, from the fluid lumen 42 flowing from a fluid source (not shown) at the proximal end 12 of the catheter 22 into the proximal end of the fluid manifold 46.

A series of blind holes 40 are spaced apart linearly along the length of the ablation electrode section 20 of the catheter 22 adjacent the position of the fluid manifold 46. The blind holes 40 only penetrate partially into the exterior wall 58 of the catheter 22. An array of smaller weep holes 38 positioned within each blind hole 40 extend through the exterior wall 58 of the catheter 22 into the fluid manifold 46, thereby providing fluid communication between the fluid manifold 46 and the blind holes 40. The blind holes 40 are sized and spaced apart from each other in order to produce a continuous linear lesion. The weep holes 38 in each blind hole 40 are similarly sized and chosen in number and arrangement to provide an appropriate volume and velocity of conductive fluid flow to create the desired lesion.

A plug 52 resides within the fluid manifold 46 and is fixed to the distal end of an adjustment shaft 50. The adjustment shaft 50 may be a wire that extends from the plug 52 proximally through the catheter 22 and ultimately through the control shaft 24 for manipulation via a handle control (not shown) attached to the handle interface 4. The adjustment shaft 50 is sized to enable it to travel the length of the fluid manifold 46. The proximal end of the fluid manifold 46 creates a fluid seal around the outer surface of the adjustment shaft 50, thereby preventing fluid within the fluid manifold 46 from traveling proximally through the catheter 22 along the length of the adjustment shaft 50.

The plug 52 is affixed to the distal end of the adjustment shaft 50. The perimeter shape of the plug 52 is the same as the cross-sectional shape of the interior wall defining the fluid manifold 46. In this manner, the plug 52 creates a fluid-tight seal as it interfaces with the interior wall of the fluid manifold 46. In the embodiment depicted in FIG. 4, the plug 52 is cylindrical in shape as is the interior wall of the fluid manifold 46. The diameter of the plug 52 is thus the same as the diameter across the interior wall of the fluid manifold 46. While a fluid seal is created between the plug 52 and the interior wall of the fluid manifold 46, the plug 52 is not affixed against the fluid manifold 46 and is able to travel the entire length of the fluid manifold 46 under the operation of the adjustment shaft 50. The plug may be formed of or coated with a layer of Teflon® to provide the desired movable sealing capabilities.

A spring electrode 54 is also housed within the fluid manifold 46. The spring electrode 54 may be in the shape of a coil and is attached at a first end to the proximal side of the plug 52 and is fixed at a second end to the proximal end wall of the fluid manifold 46. At its proximal end, the spring electrode 54 is also coupled with an electrode lead wire 44, which extends proximally through the catheter 22 to the handle interface 4 for ultimate connection with a power source (not shown). The distal end of the adjustment shaft 52 is positioned within the coil windings of the spring electrode 54. The spring electrode 54 is designed to resist compression and is sized to extend the entire length of the fluid manifold 46. In a relaxed state, the spring electrode 54 extends the entire length of the fluid manifold 46 pushing the plug 52 against the distal end wall of the fluid manifold 46 wherein the spring electrode 54 maintains a mild compressive force. In response to appropriate user control of the adjustment shaft 50, the length of the spring electrode 54 may be manipulated. If the adjustment shaft 50 is pulled proximally, the plug 52 imparts a compressive force proximally on the electrode spring 54. The adjustment shaft 50 in combination with the plug 52 thereby compresses the spring electrode 54 and thus allows the plug 52 to travel proximally within the fluid manifold 46.

As noted in a normal or non-actuated position, the spring electrode 54 is at rest in an extended position, thus pushing the plug 52 against the distal end of the fluid manifold 46. It should be noted that in addition to the force of the spring electrode 54, pressure of the conductive fluid in the fluid manifold 46 also forces the plug 52 toward the distal end of the fluid manifold 46. With the plug 52 in this distal position, the conductive fluid entering the fluid manifold 46 from the fluid lumen 42 via the transverse inlet channel 48 fills the entire length of the fluid manifold 46. Upon application of energy transmitted along the electrode lead wire 44 from an energy source, the spring electrode 54 is energized and transfers energy to the conductive fluid throughout the fluid manifold 46. The conductive fluid in the fluid manifold 46 is under pressure and thus is forced to exit the fluid manifold 46 through the weep holes 38 in the exterior wall 58 of the catheter 22. The conductive fluid exiting the weep holes 38 spreads laterally within the area of the recessed blind holes 40, even when the ablation electrode section 20 is placed directly against the target tissue to be ablated. This allows for greater surface area contact of the tissue by the energized conductive fluid exiting the catheter 22 resulting in a more even lesion.

In the example just described, each of the weep holes 38 and blind holes 40 is in fluid communication with the conductive fluid within the fluid manifold 46. Thus, ablation energy is transmitted to adjacent tissue along the entire length of the ablation electrode section 20 of catheter 22. It may, however, be desirable to create a lesion that is shorter in length than the entire length of the ablation electrode section 20. In such an instance, the clinician may actuate the adjustment shaft 50 by pulling it proximally. Proximal movement of the adjustment shaft 50 in turn pulls the plug 52 proximally, which simultaneously compresses the spring electrode 54. Because of the fluid-tight fit between the plug and the interior surface of the fluid manifold 46, the conductive fluid within the fluid manifold 46 cannot flow distally beyond the plug 52. Thus, as the plug 52 moves proximally past distally located weep holes 38 and corresponding blind holes 40, those weep holes 38 and blind holes 40 distal to the position of the plug 52 are no longer part of an active electrode array. In this manner, through the distal and proximal movement of the adjustment shaft 50, the active length of the ablation electrode section 20 of the catheter 22 can be variably adjusted by the clinician.

It should be noted that as the adjustment shaft 50 is moved proximally, a vacuum may be created in the area of the fluid manifold 46 distal to the distal end of the plug 52. As a result of this void or vacuum, blood may enter into the fluid manifold 46 via the weep holes 38 distal to the plug 52 at that particular time. This entry of blood into the catheter 22 is not considered of significant concern for at least two reasons. First, there is little likelihood of coagulum forming within the weep holes 38 or the area of the fluid manifold 46 distal to the plug 52 because the plug 52 insulates the blood from the ablation energy conducted by the spring electrode 54 on the proximal side of the plug 52. Second, when the adjustment shaft 50 is moved distally, the plug 52 forces the blood within the fluid manifold 46 distal to the plug 52 out of the fluid manifold 46 through weep holes 38 of the blind holes 40 distal to the plug 52. Further, once the plug 52 moves distally past a particular blind hole 40, the fluid within the fluid manifold 46 on the proximal side of the plug 52 forces any remaining blood within the weep holes 38 through the exterior wall 58 of the catheter 22. It may be desirable, when moving the adjustment shaft 50 distally, to cease the application of ablation energy through the electrode lead wire 44 and spring electrode 54 for a period of time in order to appropriately flush and cleanse the fluid manifold 46 as necessary.

Figure 9:
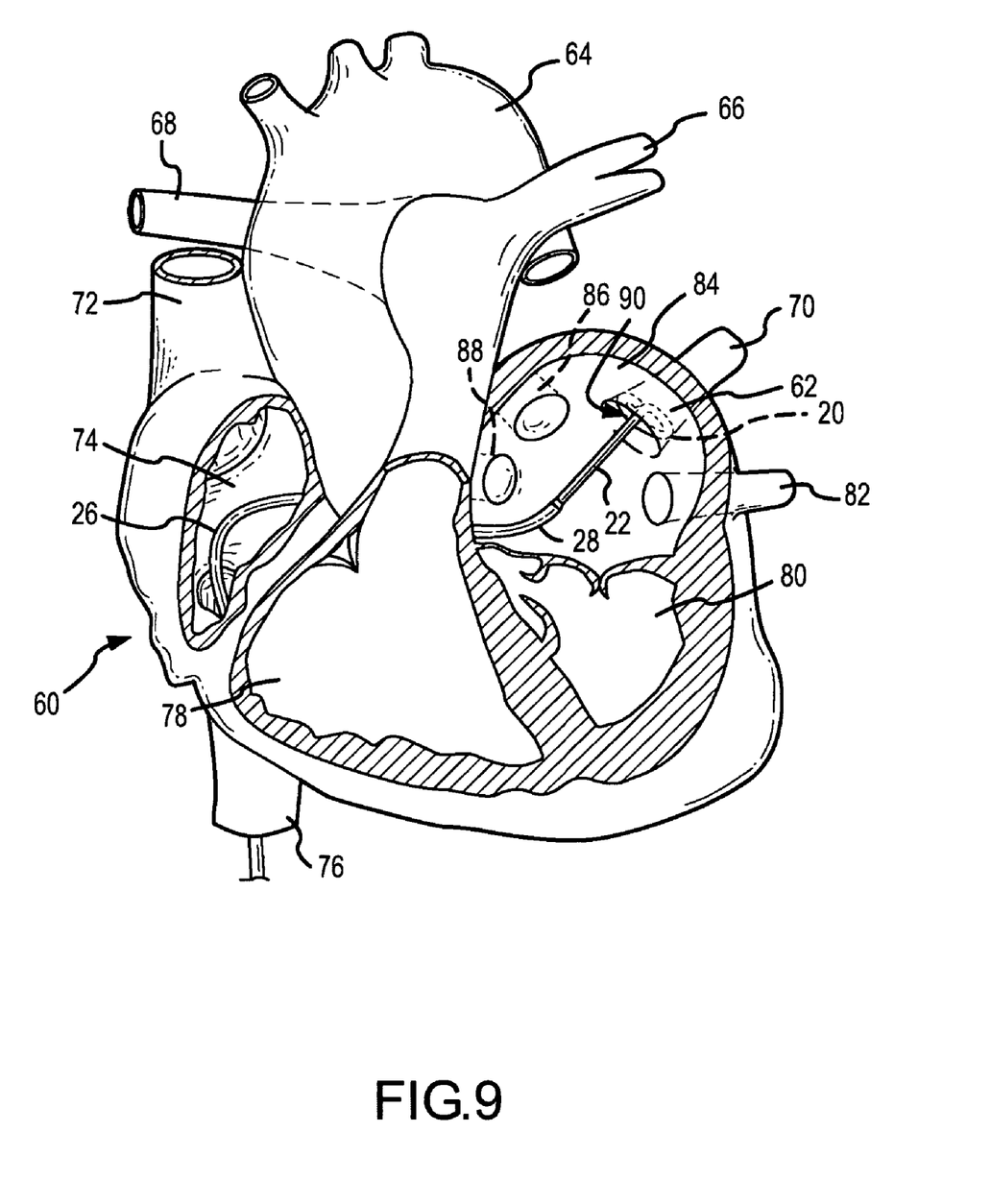
FIG. 9 is an isometric view of a heart with portions of the atria and ventricles cut-away to reveal positioning of a generic version of the catheter of the present invention in the left atrium, adjacent to the left superior pulmonary vein.

The catheter 22 may further house a shape-retention or shape-memory wire 43 in order to impart a desired shape to the distal end 12 of the catheter 22 in the area of the ablation electrode section 20. See FIGS. 4 and 6. A shape-retention or shape-memory wire 43 is flexible while a clinician negotiates the catheter 122 through the vasculature to reach the heart and enter an atrial chamber. Once the distal end 12 of the catheter 22 reaches the desired cardiac cavity with the ablation electrode section 20, the shape-retention/shape-memory wire 43 can be caused to assume a pre-formed shape form, e.g., the C-shaped configuration of the ablation electrode section 20, to accurately orient the ablation electrode section 20 within the cardiac cavity for the procedure to be performed. As shown in FIG. 9 and described later herein, the C-shaped configuration of the ablation electrode section 20 may be used to perform ablation operations at the ostia of vessels entering the atria. However, any desired shape may be imparted to the catheter through the use of such shape-retention or shape-memory wires to appropriately conform to tissue or to the shape of a cavity in order to create the desired lesion at a desired location.

In one embodiment, the shape-retention/shape-memory wire 43 may be NiTinol wire, a nickel-titanium (NiTi) alloy, chosen for its exceptional shape-memory properties. Shape-memory metals, such as NiTinol, are materials that have been plastically deformed to a desired shape before use. Then upon heat application, either from the body as the catheter is inserted into the vasculature or from external sources, the shape-memory material is caused to assume its original shape before being plastically deformed. A shape-memory wire generally exhibits increased tensile strength once the transformation to the pre-formed shape is completed. NiTinol and other shape-memory alloys are able to undergo a "martenistic" phase transformation that enables them to change from a "temporary" shape to a "parent" shape at temperatures above a transition temperature. Below the transition temperature, the alloy can be bent into various shapes. Holding a sample in position in a particular parent shape while heating it to a high temperature programs the alloy to remember the parent shape. Upon cooling, the alloy adopts any temporary shape imparted to it, but when heated again above the transition temperature, the alloy automatically reverts to its parent shape. Alternately, or in addition, shape-memory materials may also be super elastic—able to sustain a large deformation at a constant temperature—and when the deforming force is released they return to their original undeformed shape.

Common formulas of NiTinol have transformation temperatures ranging between −100 and +110° C., have great shape-memory strain, are thermally stable, and have excellent corrosion resistance, which make NiTinol exemplary for use in medical devices for insertion into a patient. For example, the shape-memory wire may be designed using NiTinol with a transition temperature around or below room temperature. Before use the catheter is stored in a low-temperature state. By flushing the fluid lumen with chilled saline solution, the NiTinol shape-memory wire can be kept in the deformed state while positioning the catheter at the desired site. When appropriately positioned, the flow of chilled saline solution can be stopped and the catheter, either warmed by body heat or by the introduction of warm saline, promotes recovery by the shape-memory wire to assume its "preprogrammed" shape, forming, for example, the C-shaped curve of the ablation electrode section.

Figure 7:
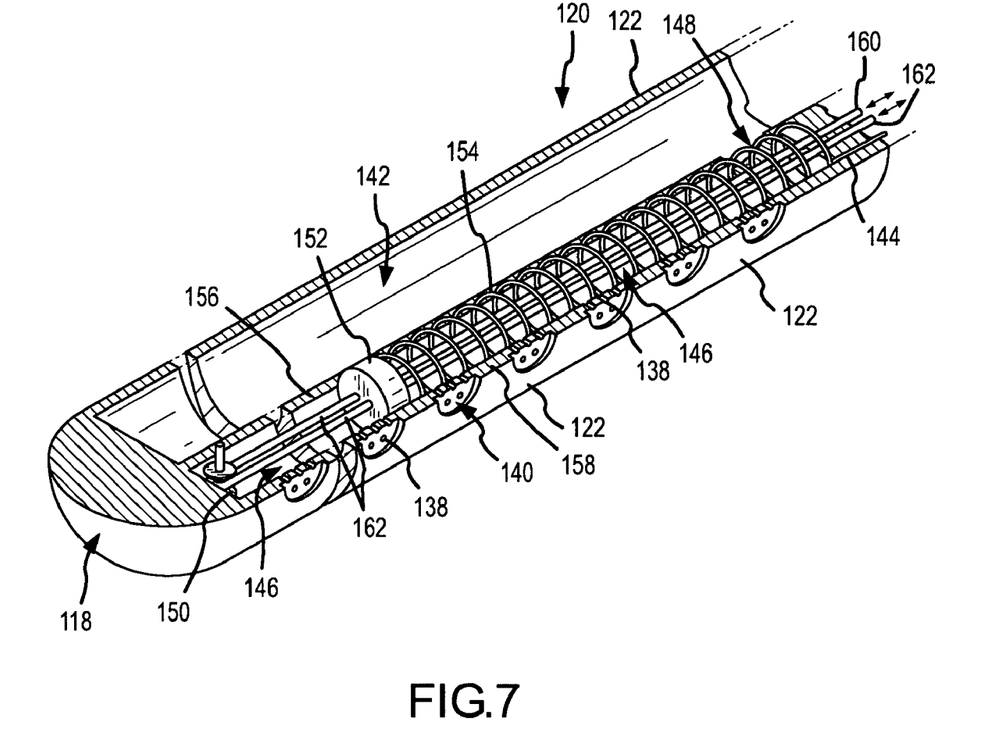
FIG. 7 is an isometric view with a partial cut-away of a second embodiment of a catheter according to the present invention.

A second embodiment of the ablation electrode structure 120 according to the present invention is depicted in FIG. 7. As in the previous embodiment, the catheter 122 defines a fluid lumen 142 extending the length of the catheter 122 from the proximal end to the distal tip 118. A fluid manifold 146 extends within the ablation electrode section 120 at the distal end of the catheter 122 parallel with the fluid lumen 142 and is separated from the fluid lumen 142 by an interior wall 156. The fluid manifold 146 is in fluid communication with the fluid lumen 142 via the transverse inlet channel 148 extending between the fluid manifold 146 and the fluid lumen 142 through the interior wall 156. The transverse inlet channel 148 is located at the proximal end of the fluid manifold 146. A linear array of blind holes 140 is formed within the exterior wall 158 of the catheter 122 opposite the side of the fluid lumen 142. Within each blind hole 140 is a collection of weep holes 138, which extend through the exterior wall 158 of the catheter 122 and which are in fluid communication with the fluid manifold 146.

As in the previous embodiment, a spring electrode 154 resides within the fluid manifold 146 and is connected to an energy source at a proximal end of the catheter 122 via an electrode lead wire 144. The proximal end of the spring electrode 154 is fixed to the catheter 122 at the proximal end of the fluid manifold 146. The distal end of the spring electrode 154 is affixed to a plug 152. The plug 152 is sized to seal against the internal walls of the fluid manifold 146, thereby preventing any of the conductive fluid entering the proximal end of the fluid manifold 146 from the fluid lumen 142 via the transverse inlet channel 148 from seeping or flowing distally past the plug 152.

A first pull wire 160 is fixed to the proximal side of the plug 152 and extends distally therefrom through the coils of the spring electrode 154 to exit the proximal end of the fluid manifold 146 and travel distally through the catheter 122 to the handle interface for manipulation by a clinician. A second pull wire 162 similarly extends proximally through the catheter 122 parallel to the first pull wire 160 and is received in the handle interface for ultimate manipulation by a clinician. The second pull wire 162 extends distally within the fluid manifold 146 and through the interior of the windings of the spring electrode 154. The second pull wire 162 extends through an aperture within the plug 152, wraps around a pulley 150 seated at the distal end of the fluid manifold 146 at the distal tip 118 of the catheter 122, and returns proximally to where it is affixed to the distal side of the plug 152. The interface between the plug 152 and the second pull wire 162 is designed to create a fluid seal between the plug 152 and the second pull wire 162 while simultaneously allowing the plug 152 to move along the second pull wire 162. A fluid seal is also created about the first pull wire 160 and the second pull wire 162 at the proximal end of the fluid manifold 146 where the first pull wire 160 and the second pull wire 162 exit the fluid manifold 166 into a proximal portion of the catheter 122.

In operation, a clinician can vary the length of an active portion of the ablation electrode section 120 of the catheter 122 by pulling either the first pull wire 160 or the second pull wire 162 proximally. When the first pull wire 160 is pulled proximally, the plug 152 moves proximally within the fluid manifold 146, thus preventing flow of conductive fluid through any of the weep holes 138 located distal to the position of the plug 152. In this manner, the effective length of the ablation electrode section 120 is shortened from the maximum allowed by the design of the ablation electrode section 120. For example, if an ablation electrode section of a catheter of the present invention were to have an array of ten blind holes and the plug were positioned proximal to two of the blind holes, only eight of the blind holes would be able to direct energized conductive fluid exiting from the corresponding weep holes to adjacent tissue for ablation.

In order to extend the length of the active section of the ablation electrode section 120, the second pull wire 162 may be pulled proximally by the clinician. The pulling force on the second pull wire 162 pulls on the distal end of the plug 152 as a result of the transference of the proximal pulling force to a distal pulling force as the second pull wire 162 wraps around the pulley 150. As the plug 152 moves proximally and distally within the fluid manifold 146, it also slides along a length of the second pull wire 162 within the fluid manifold 146. The design of the catheter 122 of FIG. 7 utilizing the first pull wire 160 and the second pull wire 162 may be desirable when utilizing a spring electrode 154 with a minimal expansive force that would otherwise be insufficient to move the plug 152 to the distal end of the fluid manifold 146 as a resting position. In an alternate embodiment (not shown), the ablation electrode section of the catheter may be designed without a spring electrode. In this embodiment, the first pull wire 160 may also perform the function of an active electrode to transfer energy from an energy source to the conductive fluid within the fluid manifold 146. Without an expansive spring force acting on the plug, the need for the combination of a first pull wire, a second pull, and a pulley in order to move the plug within the fluid lumen becomes apparent.

Figure 8:
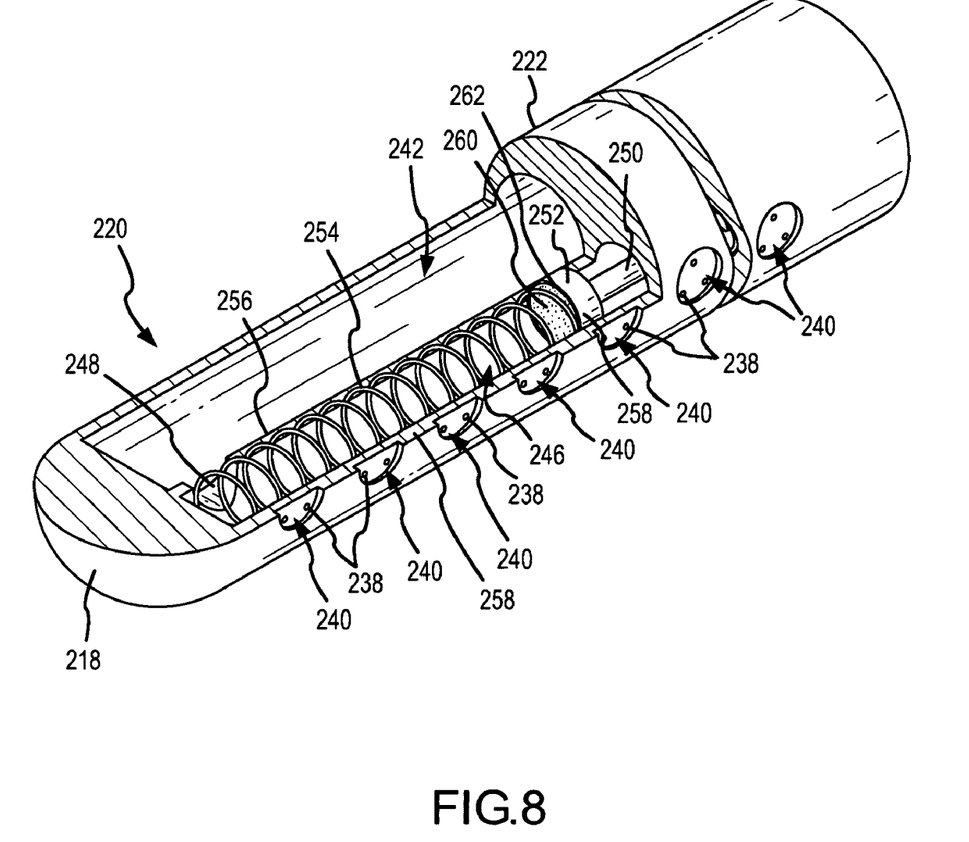
FIG. 8 is an isometric view with a partial cut-away of a third embodiment of a catheter according to the present invention.

A further embodiment of the present invention is depicted in FIG. 8. In this embodiment, a catheter 222 has an ablation electrode section 220 adjacent to the distal tip 218 of the catheter 222. A fluid lumen 242 extends from the proximal end of the catheter 222 to the distal tip 218. Adjacent the fluid lumen 242 within the catheter 222 is a fluid manifold 246. As in the previous embodiments, the fluid manifold 246 is a lumen of discrete length extending only within the ablation electrode section 220 of the catheter 222. The fluid manifold 246 is in fluid communication with the fluid lumen 242 via a transverse inlet channel 248 defined within an interior wall 256 separating the fluid lumen 242 from the fluid manifold 246. Contrary to the previous embodiments, in the present embodiment, the transverse inlet channel 248 is located adjacent the distal tip 218 of catheter 222.

The fluid manifold 246 is positioned adjacent to the exterior wall 258 of the catheter 222. A linear array of blind holes 240 are formed within the exterior wall 258 of the catheter 222 adjacent the fluid manifold 246. Within each blind hold 240, is a set of weep holes 238, which extend through the exterior wall 258 of the catheter 222. In the embodiment shown in FIG. 8, three weep holes 238 are provided per blind hole 240. However, any number of weep holes, for example, between one and ten, may be provided per blind hole. The determination of a number of weep holes per blind hole may be made based upon, for example, a desired rate of fluid flow exiting the catheter or a desired fluid pressure or velocity of the fluid flow through the weep holes.

A plug 252 is affixed to the distal end of an adjustment shaft 250 and is positioned within the fluid manifold 246. The adjustment shaft 250 extends proximally through the catheter 222 to the handle interface for manipulation by a clinician. The circumferential wall of the plug 252 seals against the interior wall of the fluid manifold 246 to prevent fluid migration proximal to the plug 252. A spring electrode 254 is positioned within the fluid manifold 246 and extends from the distal tip 218 of the catheter 222 to the distal face 260 of the plug 252. The spring electrode 254 is fixed at its distal end to the distal end of the fluid manifold 246 and at its proximal end to the distal end of the plug 252. In this embodiment, the adjustment shaft 250 acts as an electrode lead wire to transfer ablation energy from an energy source to the spring electrode 254. In this embodiment, the plug 252 is conductive and is thus both mechanically and electrically coupled with the adjustment shaft 250. The adjustment shaft 250 and the proximal side in the side walls of the plug 252 are covered with an insulating coating 262. However, the distal face 260 of the plug 252 remains uncoated and is electrically coupled with the spring electrode 254.

In operation of the embodiment of FIG. 8, the expansive force of the spring electrode 254 in its fully extended position pushes the plug 252 proximally against the proximal end of the fluid manifold 246. In this position, each of the blind holes 240 of the ablation electrode section 220 of the catheter 222 may operate as an active virtual electrode to flow energized conductive fluid against adjacent tissue to be ablated. Conductive fluid flows through the fluid lumen 242, through the transverse inlet channel 248 adjacent the distal tip 218 of the catheter 222, into the fluid manifold 246 where ablation energy is transferred from the spring electrode 254 to the conductive fluid, and exits the fluid manifold 246 via the weep holes 238 at the location of each of the blind holes 240.

To vary the length of the active portion of the ablation electrode section 220, a clinician may push the adjustment shaft 250 distally thus moving the plug 252 distally and compressing the spring electrode 254. As the plug 252 is moved distally, it arrests the flow of fluid to that portion of the fluid manifold 246 proximal to the plug 252. Thus, any blind hole 240 and its corresponding weep holes 238 positioned proximal to the position of the plug 252 is isolated from the supply of conductive fluid entering the fluid manifold 246 through the transverse inlet channel 248 at the distal end of the fluid manifold 246. Thus, the effective length of the active portion of the ablation electrode section 220 is shortened. The difference between the present embodiment of FIG. 8 and the previous embodiments described herein, is that the active portion of the ablation electrode section 220 of the present embodiment is located adjacent the distal tip 218 of the catheter 222. In contrast, in the prior embodiments, the active portion of ablation section of the catheter is spaced apart from the distal tip of the catheter when the ablation electrode section is shortened from its maximum possible length.

It should be noted that in the present embodiment, that portion of the adjustment shaft 250 extending within the fluid manifold 246 and the proximal side and sidewalls of the plug 252 are coated with electrically insulating material. It is desirable to insulate the adjustment shaft 50 and the proximal side of the plug 252 to ensure that ablation energy is not imparted to any blood that may enter into the fluid manifold 246 on the proximal side of the plug 252 when plug 252 is positioned apart from the proximal end of the fluid manifold 246. If the adjustment shaft 250 and the plug 252 are not so insulated, blood seeping through the weep holes 238 of portholes 240 positioned proximal to the position of plug 252 into the void space in the fluid manifold 246 could form coagulum within the fluid manifold 246 upon receipt of energy from an uninsulated adjustment shaft 250. The creation of such coagulum within the fluid manifold 246 would impede the movement of the adjustment shaft 250 and the plug 252 and would potentially clog the weep holes 238 of blinds holes 240 on the proximal end of the plug 252, thus preventing the egress of the conductive fluid through such blind holes 240 when the plug 252 returns to its most proximal position within the fluid manifold 246.

In an alternative embodiment of the invention (not shown), the spring electrode may be positioned proximal to the plug and affixed to the plug at its distal end. The adjustment shaft may extend within the coils of the spring electrode within the fluid manifold to attach to the proximal side of the plug. The spring electrode in this embodiment may exert a contractile force to pull the plug proximally after having been moved distally by the adjustment shaft Alternatively, the spring may not be an electrode and may merely provide the mechanical, contractile force. In this version, the adjustment shaft may function as the electrode. When the spring is in a contracted, resting position, the plug may be located adjacent to and block the transverse inlet channel, thus preventing fluid flow from the fluid lumen into the fluid manifold. Either of these embodiments may be desirable as a mechanism to prevent fluid flow through fluid manifold and out the weep holes except when an ablation procedure is actually performed in order to reduce the volume of conductive fluid introduced into the patient.

In yet another embodiment of the invention (not shown), the fluid manifold does not house a spring electrode. The plug is merely moved proximally and distally within the fluid manifold by the adjustment shaft. The adjustment shaft may be affixed to the proximal side of the plug and the transverse inlet channel may be located at either the proximal end or the distal end of the fluid manifold. If the transverse inlet channel is at the proximal end of the fluid manifold, the adjustment shaft may operate as the electrode. If the transverse inlet channel is located at the distal end of the fluid manifold, an expandable electrode positioned distal to the plug may be desirable. One possible design for such and expandable electrode is to provide a hollow adjustment shaft that houses the electrode wire. The electrode wire would extend through and aperture in the plug to the distal end of the fluid manifold. Both the plug and the adjustment shaft would travel along the electrode wire, variously exposing and concealing the wire as the plug is moved proximally and distally. Again, it is desirable to not have an active electrode wire exposed within the fluid manifold on a side of the plug opposite the volume of conductive fluid to avoid energizing any blood that may enter the fluid manifold and unnecessarily create coagulum.

FIG. 9 schematically depicts the catheter 22 and ablation electrode section 20 according to a generic embodiment of the present invention being used to ablate tissue in a left superior pulmonary vein 70. FIG. 9 includes a number of primary components of the heart 60 to orient the reader. In particular, starting in the upper left-hand portion of FIG. 9, and working around the periphery of the heart 60 in a counterclockwise fashion, the following parts of the heart 60 are depicted: the superior vena cava 72, the right atrium 74, the inferior vena cava 76, the right ventricle 78, the left ventricle 80, the left inferior pulmonary vein 82, left superior pulmonary vein 70, the left atrium 84, the right superior pulmonary vein 86, the right inferior pulmonary vein 88, the left pulmonary artery 66, the arch of the aorta 64, and the right pulmonary artery 68.

The distal end of the ablation electrode section 20 is positioned adjacent to the ostium 90 of the left superior pulmonary vein 70 using known procedures. For example, to place the ablation electrode section 20 in the position shown in FIG. 19, the right venous system may be first accessed using the "Seldinger technique." In this technique, a peripheral vein (such as a femoral vein) is first punctured with a needle and the puncture wound is dilated with a dilator to a size sufficient to accommodate an introducer (e.g., the outer guiding introducer 26 shown in FIG. 1). The outer guiding introducer 26 with at least one hemostatic valve (see FIG. 1) is seated within the dilated puncture wound while maintaining relative hemostasis. From there, the outer guiding introducer 26 is advanced along the peripheral vein, into the inferior vena cava 76, and into the right atrium 74. A transeptal sheath may be further advanced through the outer guiding introducer 26 to create a hole in the interatrial septum between the right atrium 74 and the left atrium 84.

Once the outer guiding introducer 26 is in place in the right atrium 74, the inner guiding introducer 28, housing the catheter 22 with the ablation electrode section 20 on the distal end, is introduced through the hemostatic valve 6 of the outer guiding introducer 26 and navigated into the right atrium 74, through the hole in the interatrial septum, and into the left atrium 84. Once the inner guiding introducer 28 is in the left atrium 84, the ablation electrode section 20 of the catheter 22 and may be advanced through the distal tip of the inner guiding introducer 28. The ablation electrode section 20 as shown in FIG. 19 is being inserted into the ostium 90 of the left superior pulmonary vein 70 to contact the tissue of the walls of the vein. The configuration of the ablation electrode section 20 as depicted in FIGS. 2 and 3 is advantageous for maintaining consistent contact with tissue in a generally cylindrical vessel. Other configurations of the ablation electrode section 20 may be used to greater advantage on tissue surfaces of other shapes.

While the ablation electrode 20 is in the left superior pulmonary vein 70, the ablation electrode section 20 may be energized to create the desired lesion in the left superior pulmonary vein 70. The RF energy emanating from the ablation electrode section 20 is transmitted through the conductive fluid medium, which flows through the fluid lumen, through the dispersion openings, through the porous material (depending upon the particular embodiment), through the mesh layer, and impacts the adjacent tissue. Thus, a lesion is formed in the tissue by the RF energy. The conductive fluid medium may also experience ohmic heating as it flows along either the electrode lead or through the mesh layer acting as the electrode (depending upon the particular embodiment). Lesion formation may thus also be facilitated by the conductive fluid medium, which may have been heated by ohmic heating to a sufficiently high temperature to facilitate or enhance lesion formation. The RF energy is conducted into the adjacent tissue and the heated conductive fluid convectively affects the temperature of the tissue. In order to form a sufficient lesion, it is desirable to raise the temperature of the tissue to at least 50° C. for an appropriate length of time (e.g., one minute). Thus, sufficient RF energy must be supplied to the electrode to produce this lesion-forming temperature in the adjacent tissue for the desired duration.

The length of the lesion formed may be varied by varying the active length of the ablation electrode section 20 of the catheter 22. The clinician may adjust the position of the plug within the fluid manifold to prevent the egress of energized conductive fluid from the blind holes positioned opposite the plug from the inlet of the conductive fluid into the fluid manifold. In this manner, only those blind holes positioned between the plug and the transverse inlet channel will act as an outlet for the energized conductive fluid for ablation of adjacent tissue. In this manner the length of the lesion on the target tissue may be adjusted according to the clinical need without unnecessary tissue necrosis.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A catheter with a distal ablation electrode section, the catheter comprising
    an exterior catheter wall;
    a proximal section;
    an ablation section at a distal end of the catheter;
    an interior catheter wall at least partially defining a fluid lumen extending from the proximal section to the ablation section;
    a fluid manifold at least partially defined by the interior catheter wall and the exterior catheter wall;
    wherein the fluid manifold is positioned in the ablation section adjacent to the fluid lumen and separated from the fluid lumen by the interior catheter wall; and
    wherein the interior catheter wall further defines a channel between the fluid lumen and the fluid manifold, and the interior catheter wall and the exterior catheter wall are configured such that the fluid lumen and the fluid manifold do not translate longitudinally relative to each other;
    an array of a plurality of apertures defined within the exterior catheter wall adjacent to the fluid manifold and in fluid communication with the fluid manifold;
    an electrode positioned within the fluid manifold;
    a movable sealing plug positioned within the fluid manifold; and
    an actuator attached to the movable sealing plug for repositioning the plug within the fluid manifold;
    wherein the electrode comprises a coil spring positioned between the movable sealing plug and a position of the channel in the fluid manifold.

2. The catheter of claim 1, wherein the channel is positioned at a proximal end of the fluid manifold.

3. The catheter of claim 1, wherein the channel is positioned at a distal end of the fluid manifold.

4. The catheter of claim 1, wherein each of the plurality of apertures in the exterior catheter wall further comprises at least one weep hole circumscribed by a blind hole defined in an exterior surface of the exterior catheter wall.

5. The catheter of claim 1, wherein the array of the plurality of apertures is a linear array aligned parallel with a length of the catheter.

6. The catheter of claim 1, wherein the coil spring is attached to each of the movable sealing plug and an end wall of the fluid manifold and wherein the coil spring asserts an expansive force when compressed.

7. The catheter of claim 1, wherein the coil spring is attached to each of the movable sealing plug and an end wall of the fluid manifold and wherein the coil spring asserts a contractile force when expanded.

8. The catheter of claim 1, wherein the actuator is at least partially coated with an electrically insulating coating.

9. The catheter of claim 1, wherein
    the actuator further comprises an adjustment shaft extending from the proximal section of the catheter to the ablation section;
    a distal end of the adjustment shaft is attached to the movable sealing plug; and
    the distal end of the adjustment shaft is translatable proximally and distally along a length of the fluid manifold.

10. The catheter of claim 9, wherein the adjustment shaft comprises an electrode lead that is coupled with the electrode.

11. The catheter of claim 10, wherein the adjustment shaft is at least partially coated with an electrically insulating coating.

12. The catheter of claim 10, wherein the electrode lead further comprises the movable sealing plug, which electrically couples the adjustment shaft to the electrode; and
    wherein each of the movable sealing plug and the adjustment shaft is at least partially coated with an electrically insulating coating.

13. The catheter of claim 1, wherein the actuator further comprises:
    a first pull wire extending from the proximal section of the catheter to the ablation section;
    a second pull wire extending from the proximal section of the catheter to the ablation section; and
    a pulley mounted at a distal end of the fluid manifold, wherein
        a distal end of the first pull wire is fixed to a proximal side of the movable sealing plug;
        a distal end of the second pull wire is fixed to a distal side of the movable sealing plug; and
        the second pull wire extends distally through an aperture in the movable sealing plug and engages the pulley before the distal end of the second pull wire is fixed to the movable sealing plug.

14. A catheter with a distal ablation electrode section, the catheter comprising an exterior catheter wall;
    a proximal section;
    an ablation section at a distal end of the catheter;
    an interior catheter wall at least partially defining a fluid lumen extending from the proximal section to the ablation section;
    a fluid manifold at least partially defined by the interior catheter wall and the exterior catheter wall;
    wherein the fluid manifold is positioned in the ablation section adjacent to the fluid lumen and separated from the fluid lumen by the interior catheter wall; and wherein the interior catheter wall further defines a channel between the fluid lumen and the fluid manifold, and the interior catheter wall and the exterior catheter wall are configured such that the fluid lumen and the fluid manifold do not translate longitudinally relative to each other;
an array of a plurality of blind holes defined in an exterior surface of the exterior catheter wall adjacent to the fluid manifold;
at least one weep hole circumscribed by each blind hole, wherein the at least one weep hole is in fluid communication with the fluid manifold and the respective circumscribing blind hole;
a movable sealing plug positioned within the fluid manifold;
a coil spring electrode positioned between the movable sealing plug and a position of the channel in the fluid manifold, wherein
a first end of the coil spring electrode is attached to the movable sealing plug; and a second end of the coil spring electrode is attached to an end wall of the fluid manifold; and
an adjustment shaft for repositioning the plug within the fluid manifold, wherein the adjustment shaft extends from the proximal section of the catheter to the ablation section;
a distal end of the adjustment shaft is attached to the movable sealing plug; and the distal end of the adjustment shaft is translatable proximally and distally along a length of the fluid manifold.

15. The catheter of claim 14, wherein the channel is positioned at a proximal end of the fluid manifold.

16. The catheter of claim 14, wherein the channel is positioned at a distal end of the fluid manifold.

17. The catheter of claim 14, wherein the coil spring electrode is defined by a series of windings and the distal end of the adjustment shaft is positioned within the windings.

18. A catheter with a distal ablation electrode section, the catheter comprising:
an exterior catheter wall;
a proximal section;
an ablation section at a distal end of the catheter;
an interior catheter wall at least partially defining a fluid lumen extending from the proximal section to the ablation section;
a fluid manifold at least partially defined by the interior catheter wall and the exterior catheter wall;
wherein the fluid manifold is positioned in the ablation section adjacent to the fluid lumen and separated from the fluid lumen by the interior wall; and
wherein the interior wall further defines a channel between the fluid lumen and the fluid manifold;
an array of a plurality of blind holes defined in an exterior surface of the exterior catheter wall adjacent to the fluid manifold;
at least one weep hole circumscribed by each blind hole, wherein the at least one weep hole is in fluid communication with the fluid manifold and the respective circumscribing blind hole;
a movable sealing plug positioned within the fluid manifold;
a coil spring electrode positioned between the movable sealing plug and a position of the channel in the fluid manifold, wherein
a first end of the coil spring electrode is attached to the movable sealing plug; and
a second end of the coil spring electrode is attached to an end wall of the fluid manifold;
a first pull wire extending from the proximal section of the catheter to the ablation section;
a second pull wire extending from the proximal section of the catheter to the ablation section; and
a pulley mounted at a distal end of the fluid manifold, wherein
a distal end of the first pull wire is fixed to a proximal side of the movable sealing plug;
a distal end of the second pull wire is fixed to a distal side of the movable sealing plug; and
the second pull wire extends distally through an aperture in the movable sealing plug and engages the pulley before the distal end of the second pull wire is fixed to the movable sealing plug.

19. A method for varying the length of an active portion of a virtual electrode section of an ablation catheter, the method comprising
positioning a movable plug within a fluid manifold in the virtual electrode section, wherein the movable plug seals against the fluid manifold to prevent fluid flow within the fluid manifold from one side of the movable plug to the other side of the movable plug;
introducing conductive fluid at one end of the fluid manifold through a channel connected to a fluid lumen, such that the fluid lumen and the fluid manifold do not translate longitudinally relative to each other and are partially defined by an interior catheter wall that extends substantially the length of the virtual electrode section; flowing the conductive fluid out of the fluid manifold through a plurality of apertures in an exterior wall of the ablation catheter, wherein each of the plurality of apertures is in fluid communication with the fluid manifold;
repositioning the movable plug within the fluid manifold to prevent the conductive fluid from flowing through a subset of the plurality of apertures.

20. A catheter with a distal ablation electrode section, the catheter comprising
an exterior catheter wall;
a proximal section;
an ablation section at a distal end of the catheter;
an interior catheter wall at least partially defining a fluid lumen extending from the proximal section to the ablation section;
a fluid manifold at least partially defined by the interior catheter wall and the exterior catheter wall;
wherein the fluid manifold is positioned in the ablation section adjacent to the fluid lumen and separated from the fluid lumen by the interior catheter wall which extends substantially along the length of the ablation section; and
wherein the interior catheter wall further defines a channel between the fluid lumen and the fluid manifold;
an array of a plurality of apertures defined within the exterior catheter wall adjacent to the fluid manifold and in fluid communication with the fluid manifold;
an electrode positioned within the fluid manifold, wherein an active length of the electrode is configured for variable adjustment;
a movable sealing plug positioned within the fluid manifold; and
an actuator attached to the movable sealing plug for repositioning the plug within the fluid manifold.

* * * * *